United States Patent [19]

Belli et al.

[11] Patent Number: 5,519,144
[45] Date of Patent: May 21, 1996

[54] PROCESS FOR THE PREPARATION OF ESERETHOLE

[75] Inventors: Aldo Belli; Giorgio Chiodini; Stefano Maiorana, all of Milan, Italy

[73] Assignee: Laboratorio Chimico Internazionale S.p.A., Milan, Italy

[21] Appl. No.: 347,419

[22] PCT Filed: May 28, 1993

[86] PCT No.: PCT/EP93/01353

§ 371 Date: Dec. 19, 1994

§ 102(e) Date: Dec. 19, 1994

[87] PCT Pub. No.: WO93/24455

PCT Pub. Date: Dec. 9, 1993

[30] Foreign Application Priority Data

Jun. 1, 1992 [IT] Italy ................... MI92A1348

[51] Int. Cl.⁶ ................... C07D 209/56
[52] U.S. Cl. ................... 548/429; 564/214
[58] Field of Search ................... 548/429; 564/214

[56] References Cited

FOREIGN PATENT DOCUMENTS

| | | | |
|---|---|---|---|
| 0253372 | 1/1988 | European Pat. Off. | 548/429 |
| 2261220 | 5/1993 | United Kingdom | 548/429 |

OTHER PUBLICATIONS

CA87:17297w Aliphatic . . . Fungicides. Misato et al., p. 165, 1977.
CA120:192066s Preparation . . . eserthole. Belli et al., p. 1086, 1994.
CA122:83232P EVA– . . . film. Vermeiren, p. 91, 1995.

*Primary Examiner*—Joseph K. McKane
*Attorney, Agent, or Firm*—Bucknam and Archer

[57] ABSTRACT

Eserethole of formula

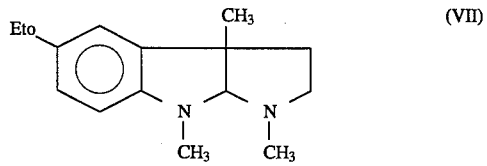

(VII)

is prepared from 1,3-dimethyl-5-hydroxy-oxindole compound II which is acylated in the first step to obtain 1,3-dimethyl-5-acyloxyoxindole (III). The product is reacted with chloroacetonitrile to obtain 1,3-dimethyl-3-cyanomethyl-5-acyloxy-oxindole (IV). The 5-acyloxy group is hydrolyzed and the hydroxy group is ethoxylated with ethyl halides or sulfate. Then the product is cyclized by treatment with sodium bis-(methoxy-ethoxy)aluminum hydride, to give O-ethyl-nor-eseroline (VI) and the compound is methylated to give eserethole (VII).

3 Claims, No Drawings

PROCESS FOR THE PREPARATION OF ESERETHOLE

This application is a 371 of PCT/EP93/01353 filed May 28, 1993.

The present invention relates to a process for the preparation of the compound of formula (II)

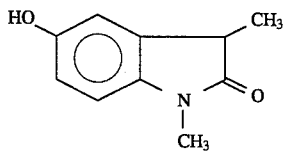

which is an useful intermediate for the preparation of eserethole.

The invention also relates to a process for the preparation of eserethole starting from compound (II).

Eserethole of formula (VII)

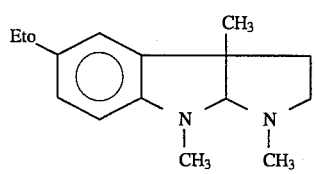

is in its turn the main intermediate for the synthesis of (−)eserine and the analogues thereof, used in human therapy for the treatment of various diseases, some of which are particularly severe and wide-spread, such as Alzheimer's disease.

(−)Eserine is a natural alkaloid which can be prepared either by extraction or synthetically.

Some of the described total synthesis involve the intermediate formation of (−) eserethole or (±)eserethole.

The interest for an industrial process to prepare eserethole and the precursors thereof which is advantageous as far as yield, purity and costs are concerned is therefore evident.

The known preparation of the intermediate of formula (II) (J. Am. Chem. Soc., 57, 563, 1935) comprises five steps, according to the following scheme I:

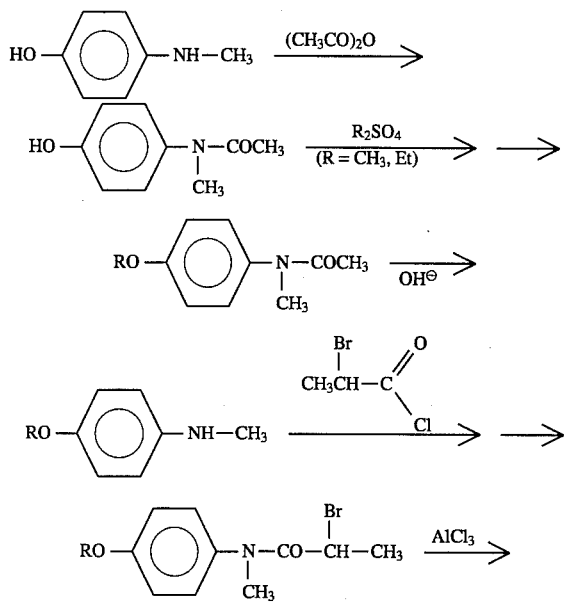

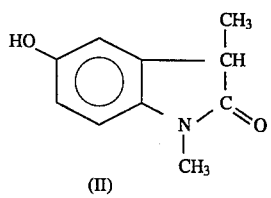

Now a process has been found, and it is the first object of the invention, which allows to prepare compound (II) in only two steps, according to the following scheme (II):

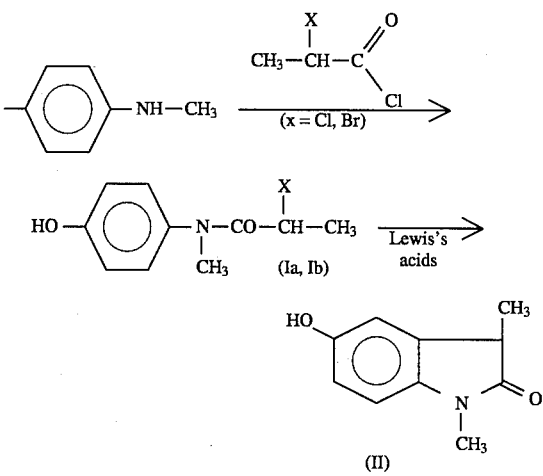

4-(N-Methylamino)phenol is reacted with a 2-halogen-propionyl chloride to give the novel intermediates of formula (Ia) (X=Cl) or (Ib) (X=Br), from which compound (II) can be obtained by cyclization in the presence of Lewis acids.

The reaction conditions and the solvents are those conventional for this kind of reactions. In the first step, toluene as the solvent and a reaction temperature of about 20° C. are particularly preferred.

In the second step, aluminium chloride is particularly preferred as the Lewis acid, whereas suitable solvents are aromatic hydrocarbons, particularly chlorobenzene.

The preparation of eserethole from compound (II) was described by a number of Authors.

Common to all the known synthesis are the O-alkylation of the intermediate (II) with alkyl sulfates and the subsequent alkylation at the 3 position of the oxindole ring with chloroacetonitrile, which alkylation can be carried out with sodium ethoxide in ethanol (Julian et al. J. Am. Chem. Soc. 57, 563, 1935) or in liquid-liquid duoble phase in the presence of chiral phase transfer catalysts (PTC) (Wong et al. J. Org. Chem. 56, (2), 873 (1991).

From the resulting compound, two reaction pathways can be followed:

i) catalytic hydrogenation of the CN group to $CH_2NH_2$ and transformation of the amine into (±) eserethole (Julian et al., ibidem; Wong et al., ibidem; Brossi et al. Heterocycles, 27(7), 1709, 1988); or ii) direct cyclization of the intermediate nitrile to nor-eseroline with lithium aluminium hydride or with sodium and alcohols and subsequent alkylation of the NH on the third ring to give eserethole (Brossi et al., Heterocycles, 27(7), 1709, 1988; Brossi et al., Heterocycles, 27(3), 745, 1988).

Now an improved process has been found, and it is a second object of the invention, for the preparation of eserethole starting from compound (II), which process comprises:

a) acylation of compound (II) to give 1,3-dimethyl-5-acyloxy-oxindole (III);

b) reaction of the compound obtained with chloroacetonitrile to give 1,3-dimethyl-3-cyanomethyl-5-acyloxy-oxindole (IV);

c) hydrolysis of the 5-acyloxy group and ethoxylation of the hydroxy group with ethyl halides or sulfate;

d) cyclization of the compound obtained in c) by treatment with sodium bis-(methoxy-ethoxy)aluminum hydride, to give O-ethyl-nor-eseroline (VI);

e) N-methylation to give eserethole (VII).

Steps b), c) and e) are carried out essentially according to the already known procedures, whereas steps a) and d) are the novel aspects of the process of the invention.

The advantage of acylation compared with alkylation resides in the higher selectivity of the reaction, without formation of double alkylation products, with a resulting increase in the yield. Particularly preferred is acylation with acetic anhydride to give intermediates (II) and (IV) in which R is acetyl. Said intermediates are novel.

In step d), the use of sodium bis-(methoxyethoxy)aluminium hydride (VITRIDE®) in toluene, instead of LiAlH$_4$ or sodium and ethanol used in the known technique, decreases the risks of a reduction process and achieves higher global yields.

N-Methylation from O-ethyl-nor-eseroline to eserethole is preferably carried out by treatment with formic aldehyde and NaBH$_4$.

The reduction with VITRIDE® can advantageously be used also on the enantiomeric mixture enriched in 1,3-dimethyl-3-cyanomethyl-5-ethoxy-oxindole which can be obtained according to Wong et al. (ibidem).

The process according to the invention is illustrated in the following scheme (III):

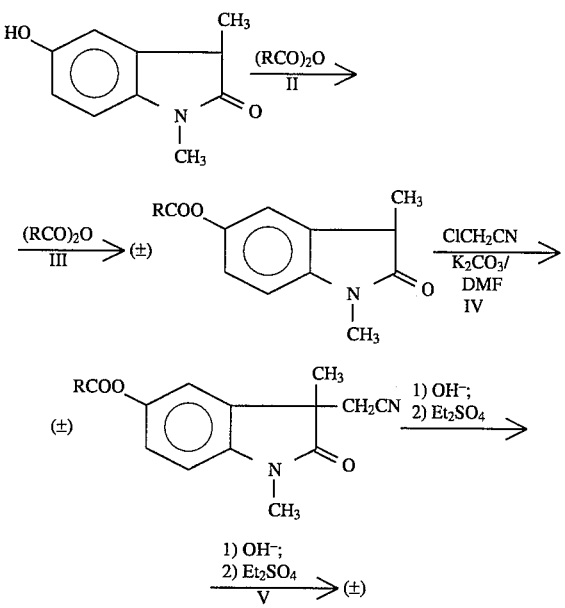

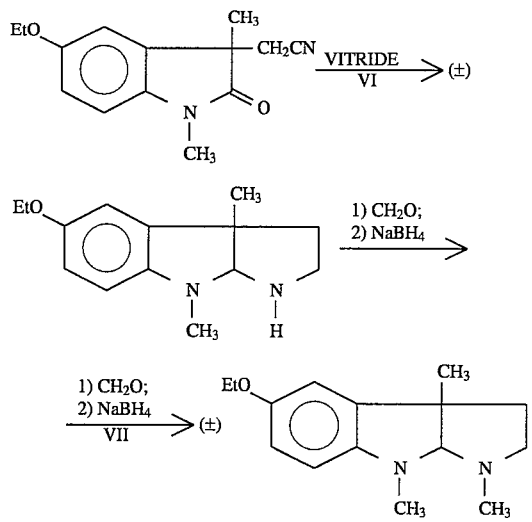

The following examples further illustrate the invention.

EXAMPLE 1

Preparation of 1,3-dimethyl-5-hydroxy-oxindole (II)

a) (±)N-Methyl-N-(4-hydroxyphenyl)-2-chloro-propionamide (Ia)

Water (320 ml), toluene (400 ml), anhydrous sodium acetate (85.6 g; 1.044 moles) and 4-(N-methylamino)phenol sulfate (METOL; 80 g; 0.2323 mole) are placed into a flask fitted with a mechanical stirrer, a thermometer and a gas tube, under nitrogen stream.

The stirred mixture is added dropwise, at 20°±2° C., with 97% 2-chloro-propionyl chloride (64 g; 0.489 mole).

The mixture is stirred for 30 minutes, then the aqueous phase is separated. The organic phase is added with 1N NaOH to pH=7, heated to 40° C. and separated from water. The organic phase is washed again with water, dried over anhydrous Na$_2$SO$_4$ and evaporated to dryness. The residue is redissolved in warm toluene (200 ml) and cooled to 0° C. (Ia) cristallyzes from the solution, it is filtered, dried in oven at 40° C. overnight.

84.7 g of (Ia) are obtained; 85% yield. M.p. 117°–119° C.

(Ia) was identified and characterized by I.R., H$^1$NMR, mass spectra and elementary analysis.

b) (±) 1,3-Dimethyl-5-hydroxy-oxindole (II)

Chlorobenzene (ml 100) and anhydrous aluminium chloride (156 g; 1.17 moles) are placed into a flask fitted with a mechanical stirrer, a thermometer and a cooler, at room temperature; the mixture is heated to 110 ° C. Keeping temperature at 110°–115 ° C., a solution prepared dissolving at about 70° C. (Ia) (100 g; 0.468 mole) in chlorobenzene (150 ml) is added thereto. The resulting mixture is then refluxed for 4 more hours.

Thereafter, the solution is cooled to about 80°14 90° C., poured into a water-ice mixture and the pasty solid is filtered.

The solid is triturated in warm ethyl acetate (350 ml), filtered, dried in oven under vacuum overnight.

77.5 g of (II) are obtained; m.p. 212°–214° C. (lit. 219° C.). 93.5% yield. (II) was identified by I.R., H$^1$NMR, mass spectra and by comparison with an authentic sample.

EXAMPLE 2

Preparation of eserethole a) (±) 1,3-Dimethyl-5-acetoxy-oxindole (III)

Glacial acetic acid (50 ml), acetic anhydride (68.7 g; 0.674 mole) and (II) (75 g; 0.421 mole) are placed into a flask, at room temperature. The suspension is added with 96% $H_2SO_4$ (3 g) and the mixture is heated to 75° C. for 30 minutes. Without cooling, the solution is slowly poured into water-ice (500 ml), stirred for 30 minutes, the solid is filtered and dried in oven under vacuum at 40° C. overnight.

80.6 g of (III) are obtained; 87% yield. M.p. (from methanol) 117°–118° C. The product was identified and characterized by I.R., $H^1NMR$, mass spectra and elementary analysis.

b) (±) 1,3-Dimethyl-3-cyanomethyl-5-acetoxy-oxindole (IV)

Dimethylformamide (240 ml), (III) (80 g; 0.365 mole), chloroacetonitrile (31.7 g; 0.417 mole) and tetrabutylammonium bromide (8 g; 0.248 mole) are placed into a flask fitted with a mechanical stirrer, at room temperature. The solution is warmed to 35° C. and added portionwise, in about 2–3 hours, with powdered anhydrous potassium carbonate (60.4 g; 0.438 mole).

The suspension is then kept under stirring at 35° C. overnight, poured into water (500 ml) and extracted twice with toluene (2×250 ml).

The organic extract is washed with water, dried over anhydrous $Na_2SO_4$, evaporated to dryness.

89 g of (IV) are obtained; 94% yield. M.p. (from methanol) 108°–109° C. (IV) was identified and characterized by I.R., $H^1NMR$, mass spectra and elementary analysis.

c) (±) 1,3-Dimethyl-3-cyanomethyl-5-ethoxy-oxindole (V)

Isopropanol (270 ml) and (IV) 89 g (0.345 mole) are placed into a flask fitted with a mechanical stirrer. The mixture is heated to 45° C. and 30% NaOH (110 g; 0.86 mole) is added in about 45–60 minutes. The solution is stirred for 30 minutes then diethyl sulfate (84.7 g; 0.55 mole) is slowly added, in about 2 hours, checking the pH of the solution to be constantly alkaline. The resulting solution is kept under stirring overnight, then cooled to 20° C. and slowly poured into water-ice (2000 ml). The solid is filtered, washed with water and dried in oven under vacuum at 40° C. overnight.

70.6 g of (V) are obtained; 84% yield. M.p. (from isopropanol) 109°–110° C. (lit. 109° C.). The product was identified and characterized by I.R., $H^1NMR$, mass spectra and by comparison with an authentic sample.

d) (±)O-Ethyl-nor-eseroline (VI)

Anhydrous toluene (270 ml) and 70% sodium bis-(2-methoxy-ethoxy)aluminum hydride (VITRIDE; 134 g; 0.464 mole) are placed into a perfectly dry flask, under nitrogen atmosphere. Intermediate (V) (53.3 g; 0.218 mole) is added portionwise, at a temperature of 25°± 3 ° C., in about 2–2,5 hours. The resulting solution is stirred at 25° C. for 30 minutes then heated to 70° C. for 2 hours. After cooling to room temperature, the mixture is poured into 1N NaOH (400 ml) and the aqueous phase is separated and extracted again with toluene (150 ml). The combined organic phases are washed with water, dried over anhydrous $Na_2SO_4$ and evaporated to dryness The residual oil is taken up with water (300 ml) and n-heptane (300 ml). The aqueous phase is separated, the organic phase is dried over anhydrous $Na_2SO_4$ and evaporated to dryness.

45 g of crude (VI) are obtained as a reddish oil which is used directly in the subsequent step.

e) (±) Eserethole (VII)

Methanol (600 ml), crude (VI) (40 g) and paraformaldehyde (21.5 g; 0.72 mole) are placed into a flask, under nitrogen, at room temperature.

The mixture is refluxed for 1 hour, then cooled to 20° C. and solid sodium borohydride (9.7 g; 0.255 mole) is added portionwise, during about 1,5–2 hours. The resulting solution is stirred at 20° C. for one hour, then the solvent is removed under vacuum.

The residue is added with water, then extracted with n-heptane (3×200 ml).

The organic extract is washed with water, dried over anhydrous $Na_2SO_4$, evaporated to dryness. The residue is dissolved in acetone (400 ml), added with d,l-tartaric acid (21.5 g; 0.143 mole) and stirred for 2 hours. The resulting solid is filtered and dried in the air.

36 g of (±)eserethole d,l-tartrate are thus obtained.

The salt is dissolved in water, alkalinized with 1N NaOH and extracted with n-heptane (3×200 ml). The organic extract is washed with water, dried over anhydrous $Na_2SO_4$ and evaporated to dryness.

21.6 g of racemic eserethole are obtained (45% yield calculated on (V)) as a yellow oil which solidifies with time, m.p. 36°–38° C.

The product was identified and characterized by I.R., $H^1NMR$, mass spectra and elementary analysis and by comparison with an authentic sample.

We claim:

1. A process for the preparation of eserethole of formula

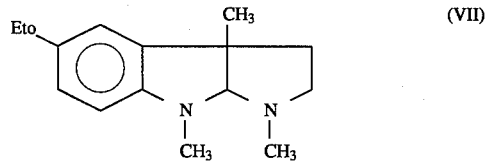

which comprises the steps of:
   a) acylating the compound II 1,3-dimethyl-5-hydroxy-oxindole to obtain 1,3-dimethyl-5-acyloxy-oxindole (III);
   b) reacting said compound (III) from step a) with chloroacetonitrile to obtain 1,3-dimethyl-3-cyanomethyl-5-acyloxy-oxindole (IV);
   c) hydrolyzing the 5-acyloxy group and ethoxylating the hydroxy group with ethyl halides or sulfate;
   d) cyclizing said compound obtained in step c) by treatment with sodium bis-(methoxy-ethoxy)aluminum hydride, to obtain O-ethyl-nor-eseroline (VI) and
   e) N-methylating said compound VI from step d) to obtain eserethole (VII).

2. The process according to claim 1 wherein said compound (II) in step a) is acetylated with acetic anhydride.

3. The compound of formula Ia of formula

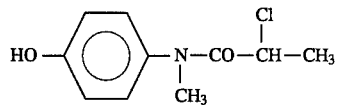

or formula Ib

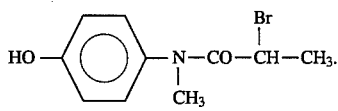

* * * * *